(12) United States Patent
Koshikawa

(10) Patent No.: US 6,569,088 B2
(45) Date of Patent: May 27, 2003

(54) ENDOSCOPE APPARATUS

(75) Inventor: Yutaka Koshikawa, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 171 days.

(21) Appl. No.: 09/727,774

(22) Filed: Dec. 4, 2000

(65) Prior Publication Data

US 2001/0003142 A1 Jun. 7, 2001

(30) Foreign Application Priority Data

Dec. 3, 1999 (JP) .......................................... 11-344785

(51) Int. Cl.⁷ .................................................. A61B 1/06
(52) U.S. Cl. ...................... 600/177; 600/176; 600/160; 600/178; 600/182; 348/68
(58) Field of Search .............................. 600/177, 176, 600/160, 178, 179, 180, 182, 108, 129; 348/68, 67

(56) References Cited

U.S. PATENT DOCUMENTS

| | | | | |
|---|---|---|---|---|
| 4,834,071 A | * | 5/1989 | Hosoi et al. ................. | 600/180 |
| 4,868,645 A | * | 9/1989 | Kobayashi ................... | 600/180 |
| 4,967,269 A | * | 10/1990 | Sasagawa et al. ........... | 600/180 |
| 4,986,262 A | * | 1/1991 | Saito ........................... | 600/108 |
| 4,998,971 A | * | 3/1991 | Fukunishi ................... | 600/108 |
| 5,042,915 A | * | 8/1991 | Akutsu et al. .............. | 600/180 |
| 5,090,400 A | * | 2/1992 | Saito ........................... | 600/108 |
| 5,536,236 A | * | 7/1996 | Yabe et al. ................... | 600/129 |
| 5,749,830 A | * | 5/1998 | Kaneko et al. ............. | 600/160 |
| 5,957,834 A | * | 9/1999 | Mochida ...................... | 600/180 |
| 6,387,044 B1 | * | 5/2002 | Tachibana et al. .......... | 600/177 |

FOREIGN PATENT DOCUMENTS

JP          10 288742          10/1998

* cited by examiner

Primary Examiner—Teresa Walberg
Assistant Examiner—Fadi H. Dahbour
(74) Attorney, Agent, or Firm—Armstrong, Westerman & Hattori, LLP

(57) ABSTRACT

An endoscope apparatus for reducing a halation for a large observation area without an illumination nonuniformity includes an insertion part which has an end having a wide-angle object optical system with two or more types of illumination optical systems having different illumination strength or light distribution. An illumination optical system having a greater illumination strength or wider light distribution is arranged on both sides of the end in a direction of a long side of a screen of the wide-angle object optical system. An illumination optical system having a lesser illumination strength or narrower light distribution is arranged on both sides of the end in a direction of a short side of the screen of the wide-angle object optical system.

16 Claims, 18 Drawing Sheets

FIG. 10(a)　　　FIG. 10(b)　　　FIG. 10(c)
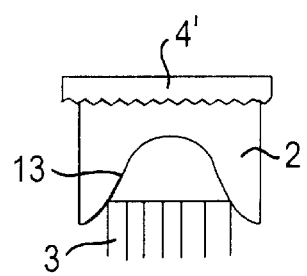 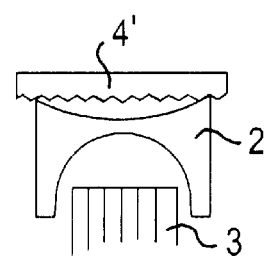 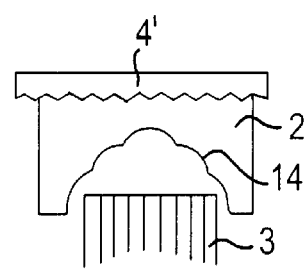
FIG. 11(a)　　　FIG. 11(b)
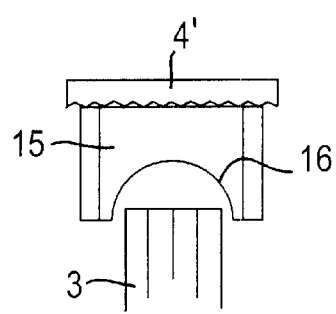 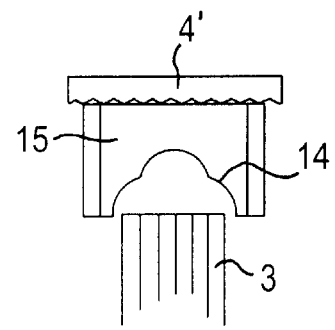

FIG. 13
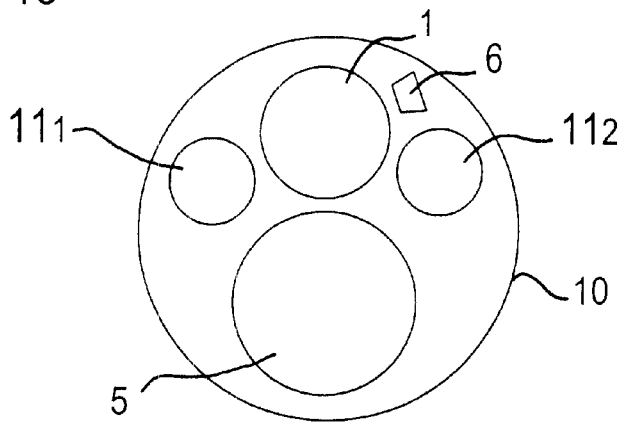
FIG. 14(a)　　　FIG. 14(b)
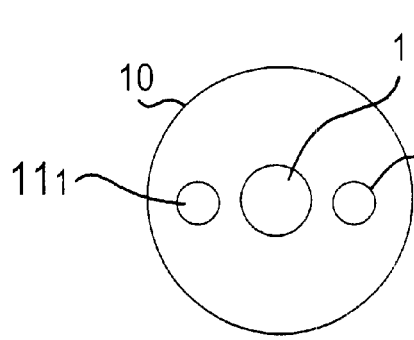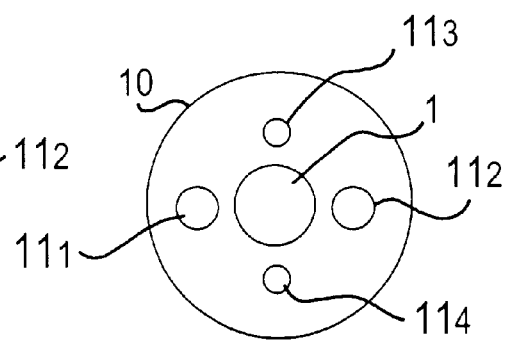
FIG. 15(a)　　　FIG. 15(b)
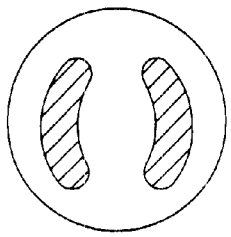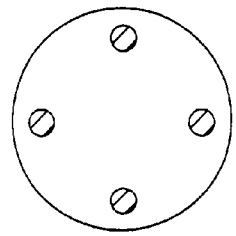

ENDOSCOPE APPARATUS

FIELD OF THE INVENTION

This invention relates to an endoscope apparatus, more specifically to an endoscope apparatus with a reduced halation, a large observation area, and without an illumination nonuniformity.

BACKGROUND OF THE INVENTION

An endoscope has been used in a broad number of fields, including the medical field to observe and diagnose the intra-corporeal of a human being. In addition, an endoscope has been used extensively, in the industrial field since a condition inside a machine can be observed and inspected without any endoscope interference.

An endoscope includes an object optical system for observing the intra-corporeal of a human beings and the interior of a machine, and an illumination optical system for illuminating an observation object. An illumination optical system consists of a light guide for transmitting the light from a light source to the tip end of the endoscope, and an illumination lens for extending a light distribution.

Moreover, it is well known to replace an illumination lens with frosted glass having a diffusion effect on supplied light. For example, FIG. 29(a) shows an illumination optical system which has a light guide 51 and a frosted glass 52, whereas FIG. 29(b) shows an illumination optical system which has a light guide 51 and an illumination lens 53.

In an endoscope observation, when an object having an intricate structure located inside a machine is observed, the brightness of the object within a visual field varies extremely due in part to the difference distances from the object, or the differences in the objective reflecting rate. When the dynamic range of the image pick-up element of an object optical system is not able to permit a certain brightness ratio, a part of the monitor screen might become white (hereinafter referred to as "halation"), which may interfere the observation.

A halation arises in the following cases: where illumination light is turned into direct reflected light by an object with a high reflecting rate, and the strong direct reflected light is then irradiated back into the object optical system; where an extreme illumination nonuniformity is generated when the illumination optical system at an end of the endoscope gets close to the object; and where both the above phenomena occur simultaneously.

In the medical field, a halation notably occurs when the object is pipe shaped, has multiple pleats is accompanied by waviness, for example, the large intestines.

That is, as shown in FIG. 30, when the endoscope end 55 is inserted in a pipe 54 with waviness and a waviness part 57, the pipe 54 exists close to an illumination optical system 56. The illumination light generated from the illumination optical system 56 is reflected on the waviness part 57 thereby generating a halation due to an extreme illumination nonuniformity. The wider the observation range of an object optical system is, that is, the larger the viewing angle a wide-angle object optical system has, the more often a halation will be generated.

The reason for the above is that, when an inner wall of a pipe and an endoscope get closer, in other words, when an illumination optical system and a range which performs a direct reflection (for example, a pleat of the large intestine) become close, strong reflected light is generated. The wider the angle object optical system has, the easier the reflected light irradiates into a visual field.

In an endoscope which has a wide-angle object optical system, a technique for preventing a halation, is described Japanese Patent Laid-Open Publication No. Hei 10-288742. The patent discloses an endoscope having an object optical system which can observe in a longitudinal direction as well as through a side of an endoscope simultaneously, by a illumination means illuminating the side. The diffusion means as the illumination means is indicated in FIG. 31, where FIG. 31(a) is a horizontal sectional view of the end part visual field of an endoscope, and FIG. 31 (b) shows the vertical sectional view thereof.

In FIG. 31(a), an object optical system 59 is provided such that it may exist in the center of an end part 58 of the endoscope. An optical axis of the radiation end of a light guide 60 which constitutes a front illumination optical system is arranged to be approximately parallel to the optical axis of the object optical system 59 so that the light side 60 illuminates a front visual field. The object optical system 59 has light guides 61 and 62 which constitute side illumination optical systems which illuminate side visual fields, respectively. Moreover, a frosted glass 63 is provided at the end of each the light guides 61 and 62 of the side illumination optical systems.

With this structure, since the illumination light in the pipe inner wall surface can irradiate uniformly even when the diffusion effect of an illumination light becomes high and it observes the pipe of a narrow diameter, the halation by the illumination light is seldom generated. Thus, in the Japanese Patent Laid-Open Publication No. Hei 10-288742, the frosted glass is provided at the end of the light guide which is a side illumination optical system so that the frosted glass is made to permeate the illumination light radiated from a light guide, thereby preventing halation by creating a diffusion effect.

However, in the case of simply arranging the frosted glass 63, as a diffusion plate, at the end of each of the light guides 61, 62, the light distribution range of the illumination light was narrow compared with that of the emitted light of an illumination optical system having a lens, so that it was easy to produce an illumination nonuniformity in a periphery of the visual field, and the periphery of the visual field became dark and was inadequate for observation.

Moreover, the illumination light distribution can be made wider only with illumination lenses, such as a concave lens. However, since the illumination light was not uniform, a halation occurred.

SUMMARY OF THE INVENTION

In view of the foregoing disadvantages inherent in the known prior art systems, the present invention solves the above-mentioned problems. Thus, it is an object of the present invention to provide an endoscope apparatus which can eliminate illumination nonuniformity and reduce halations so as to enable the endoscope apparatus to observe a wider range of an object.

In order to achieve the aforementioned objects, in a first aspect of the present invention, in an endoscope apparatus without an illumination nonuniformity, with a reduced halation and an observable large area, an end of the insertion part of an endoscope comprises a wide-angle object optical system, with two or more types of illumination optical systems having different illumination strength and light distribution. When illuminating the visual field range the illumination optical system having the greater illumination strength or light distribution among the illumination optical systems is arranged in the end position of the endoscope at both the sides of a long side of a screen of the wide-angle object optical system. At both of the sides of a short side of the screen of the wide-angle object optical system, the illumination optical system having a smaller illumination strength or a narrow light distribution is arranged among the illumination optical systems.

It is preferable that the illumination optical system consists of four illumination lenses.

It is desirable that the illumination optical system consists of a lens system which has a power and a diffusion element arranged at the object side. The lens system which has a negative power comprises a concave lens system which has a negative power and a diffusion element arranged at the object side.

It is also desirable that the lens system which has a power comprises a convex lens system which has a positive power, and a diffusion element arranged at the object side.

It is preferable that the effective area of the radiation surface of the diffusion element is larger than the effective area of the plane of incidence of the lens system.

It is desirable that the end of an endoscope have a streamline shape and an object optical system, and consists of a lens system which has a power in the direction of a slope of the streamline shape, and a diffusion element arranged at the radiation side wherein, the following conditions are fulfilled:

$$1 < Ss/Si < 8 \tag{1}$$

$$\theta p < \theta i < \theta o - \theta p \tag{2}$$

wherein Ss is the effective area of the radiation surface of the diffusion element;

Si is the effective area of the plane of incidence of the illumination lens system;

$\theta p$ is the angle between the optical axes of the object optical system and the illumination optical system;

$\theta i$ is a half-angle of the light distribution angle of the emitted light from the illumination optical system; and $\theta o$ is a half-angle of view of the object optical system.

In a second aspect of the endoscope apparatus without an illumination nonuniformity, with a reduced halation and an observable large area comprising a wide-angle object optical system, when illuminating the visual field range the illumination optical system having the greater light distribution and illumination strength is arranged among the illumination optical systems at the end position of endoscope corresponding to both sides of a long side of a screen of the wide-angle object optical system.

At the end position of the endoscope corresponding to both sides of the direction of a short side of the screen of the wide-angle object optical system, the illumination optical system having a narrow light distribution and small illumination strength is arranged among the illumination optical systems.

The illumination optical system consists of four illumination lenses.

The illumination optical system consists of a lens system which has a power, and a diffusion element arranged at the object side.

The illumination optical system consists of a concave lens system which has a negative power, and a diffusion element arranged at the object side.

The illumination optical system consists of a convex lens system which has a positive power and a diffusion element arranged at the object side.

The effective area of the radiation surface of the diffusion element is larger than the effective area of the plane of incidence of the lens system.

The end of the endoscope has a streamline shape and an object optical system, and comprises a lens system which has a power in the direction of a slope of the streamline shape, and a diffusion element configured at the radiation side wherein, the following conditions are fulfilled:

$$1 < Ss/Si < 8 \tag{1}$$

$$\theta p < \theta i < \theta o - \theta p \tag{2}$$

wherein Ss is the effective area of the radiation surface of the diffusion element;

Si is the effective area of the plane of incidence of the illumination lens system;

$\theta p$ is a angle between the optical axes of the object optical system and the illumination optical system;

$\theta i$ is a half-angle of the light distribution angle of the emitted light from the illumination optical system; and $\theta o$ is a half-angle of view of the object optical system.

BRIEF DESCRIPTION OF THE DRAWINGS

FIGS. 10(a)–(c) illustrate different modifications of an illumination lens.

FIGS. 11(a) and 11(b) illustrate additional different modifications of an illumination lens.

FIG. 13 shows an example of the layout an end layout of an endoscope.

FIGS. 14(a) and 14(b) illustrate an end layout having two and four illumination optical systems, respectively.

FIGS. 15(a) and 15(b) illustrate the state of a halation according to FIGS. 14(a) and 14(b), respectively.

DETAILED DESCRIPTION OF THE PREFERRED EMBODIMENTS

An endoscope according the first embodiment will be discussed with reference to FIGS. 1–12.

Figure 2:
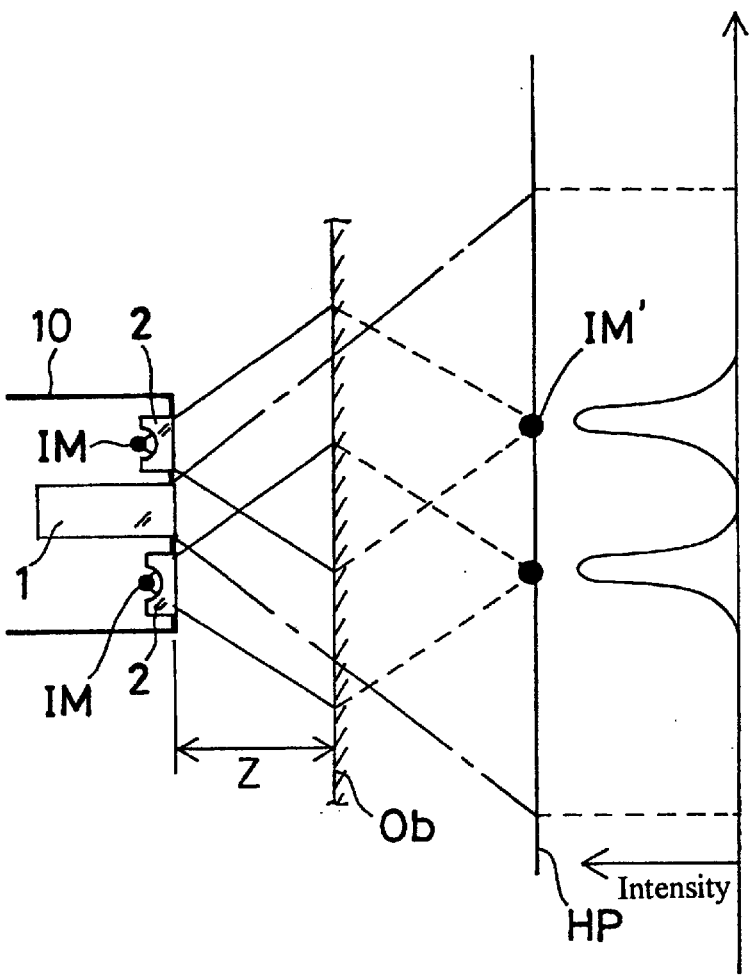
FIG. 2 illustrates generation of a halation in an endoscope.

In FIG. 2, when a object Ob, which has a very high reflecting rate, almost that of a mirror surface, is observed in front of a illumination lens 2 in the leading end part 10 of an endoscope, an object optical system 1 observes the endoscope end reflected by the mirror surface. In other words, it is equivalent to observing a virtual surface HP.

Figure 3:
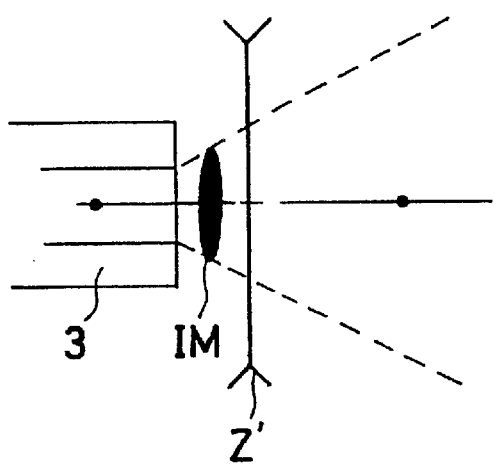
FIG. 3 illustrates an image of a light guide radiation surface when an illumination optical system is a concave lens.

Moreover, when a concave lens 2' is used as the illumination lens 2, if the image produced by concave lens 2' of the radiation surface (pupil) of a light guide 3 is considered as a secondary light source, IM as shown in FIG. 3, it is equivalent to observing image IM' of the secondary light source IM. Therefore, a very bright part arises on an observation range, as shown by the intensity of the light distribution in the right-hand side of FIG. 2.

This large difference in brightness will exceed the dynamic range of an image pick-up element, and a halation will arise.

Moreover, when the observation distance is small, that is, when z in FIG. 2 is small, most observation ranges can not be observed because of a halation.

Figure 1:
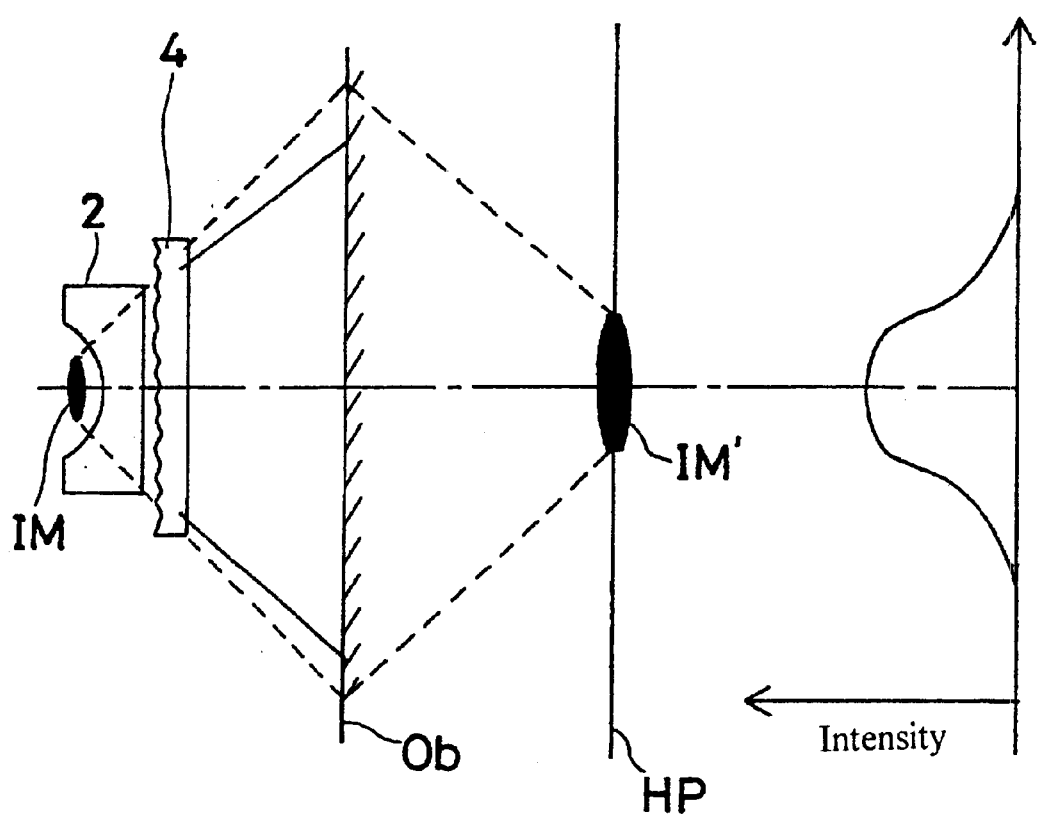
FIG. 1 illustrates an illumination optical system of an endoscope according to a first embodiment of the present invention.

Herein, one form of this Example is shown in FIG. 1.

In order to prevent a halation, a diffusion element 4, e.g., frosted glass, is arranged on the radiation side of the illumination lens 2, as shown in FIG. 1. Virtual image IM' of the radiation surface of a light guide is diffused on virtual surface HP by the diffusion element 4, and the peak value of the illumination strength falls. Therefore, by making the brightness of an observation range more uniform, it may fit within the dynamic range of an image pick-up element, and a halation can be prevented.

Figure 4:
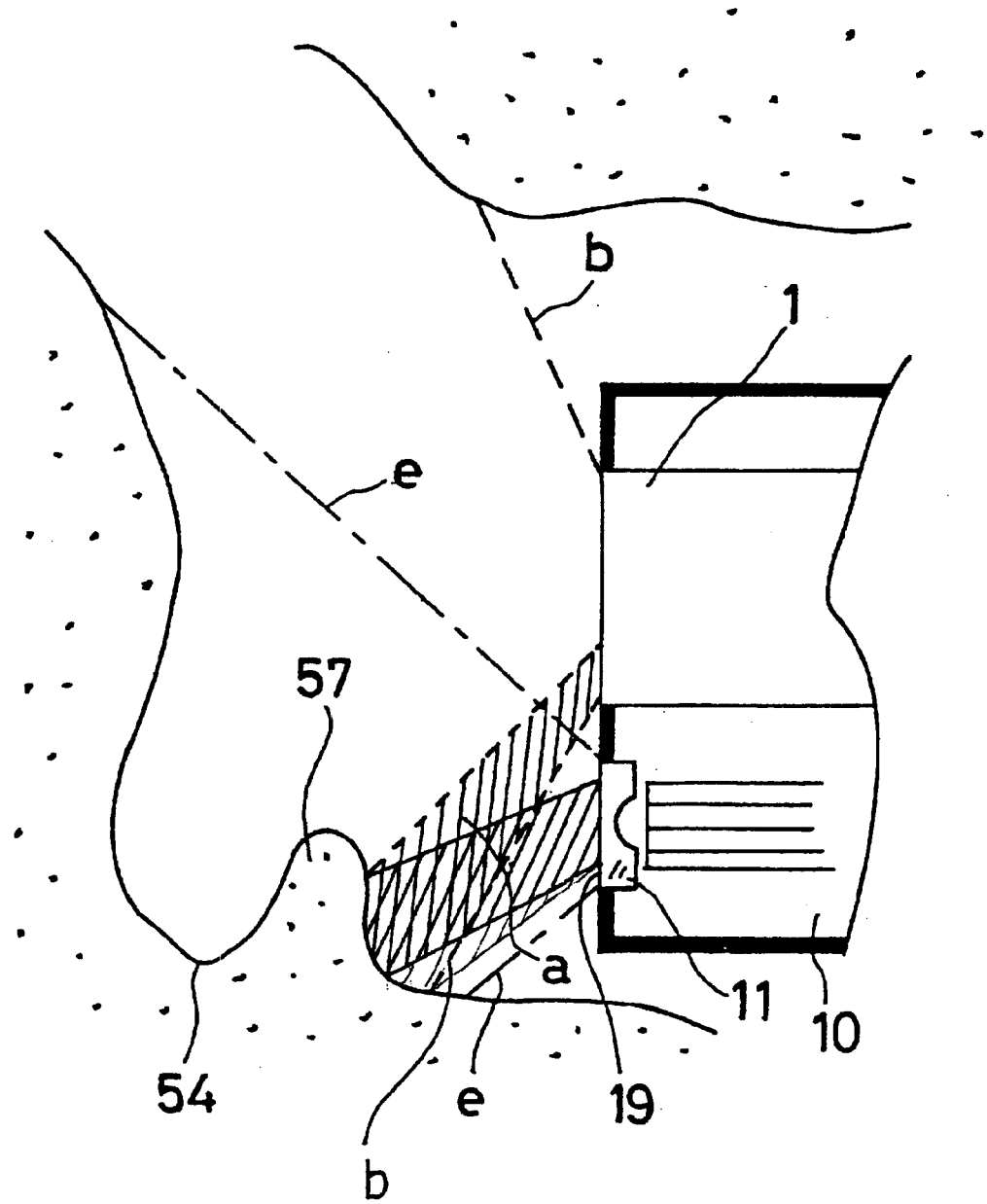
FIG. 4 illustrates the generation of a halation during an observation of a waviness part of a large intestine.

A case where a halation arises during an observation in a tubular cavity is shown in FIG. 4. FIG. 4 illustrates the case where a halation arises in a waviness part 57, when an end part 10 of an endoscope is inserted in a pipe 54 having waviness.

In FIG. 4, oblique lines show light flux which causes a halation. The light flux is part of an illumination light. The light flux radiates from an illumination optical system 11, which consists of a concave lens, and goes into the visual field range of an object optical system 1 (the is range shown by dotted lines b in FIG. 4).

Figure 6A:
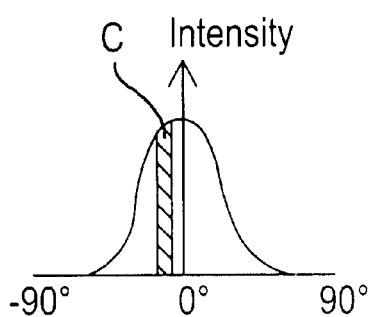
FIGS. 6a and 6b illustrate a light distribution of the illumination light according to a conventional case and the endoscope of FIG. 5, respectively.

A light distribution of the illumination light by which an observation is performed by the illumination optical system 11 is shown in FIG. 6(a). The light flux component of dot oblique line part a of the FIG. 4 corresponds to the illumination light which has the angle component of oblique line part c of FIG. 6(a).

A halation can be reduced by making the strength of an angle component of the light flux small to an entire illumination light, as shown in FIG. 5.

Figure 5A:
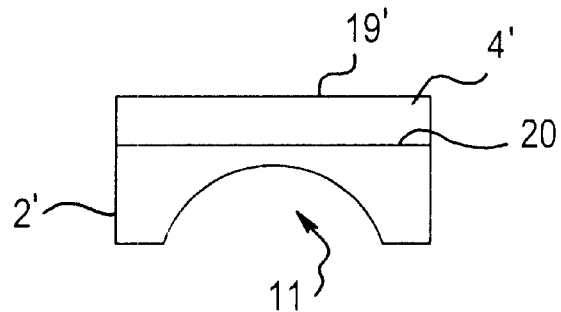
FIGS. 5a and 5b illustrate a sectional drawing and perspective diagram of the illumination optical system of the endoscope according to the first embodiment of the present invention, respectively.
Figure 5B:
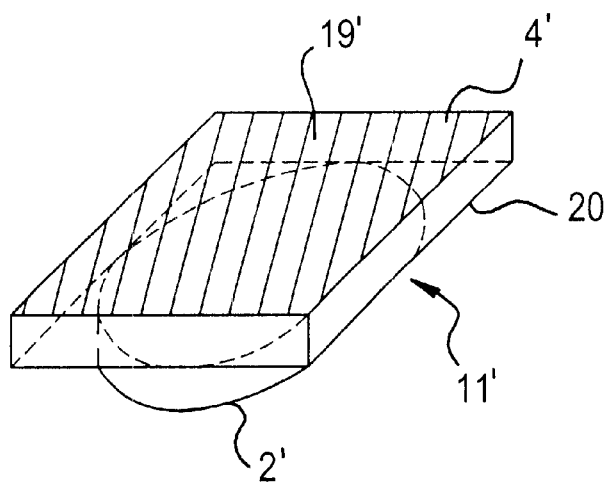
Figure 6B:
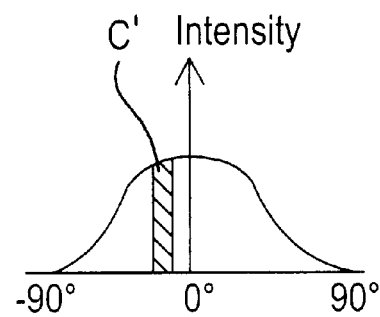

In an illumination optical system according to the first embodiment of the present invention, as shown in a sectional view in FIG. 5(a), and in a perspective diagram in FIG. 5(b), when the illumination optical system 11 is replaced with an illumination optical system 11' having a diffusion element, such as a frosted glass 4' which faces a grain surface 20 on the concave lens 2' side for illumination, an illumination light distribution, as shown in FIG. 6(b), is realized on account of the diffusion effect by the diffusion element, such as frosted glass 4'. Therefore, under the same observation conditions as shown in FIG. 4, the ratio of illumination light c' which causes a halation is less than in the illumination optical system 11 which only includes the concave lens of FIG. 4. Therefore, a halation is mitigable.

In the case of a wide-angle object optical system, since an observation power is small, and the depth of field is large, an end of the endoscope can come within a close proximity to an object. However, in this situation it is easy to produce a halation as mentioned above.

When the reflective part which causes a halation of an illumination optical system and a photographed object approach each other, the relationship of an illumination optical system and a halation may consider not only a light distribution but a position distribution (brightness distribution) of the light in the radiation surface of the illumination optical system.

Figure 7:
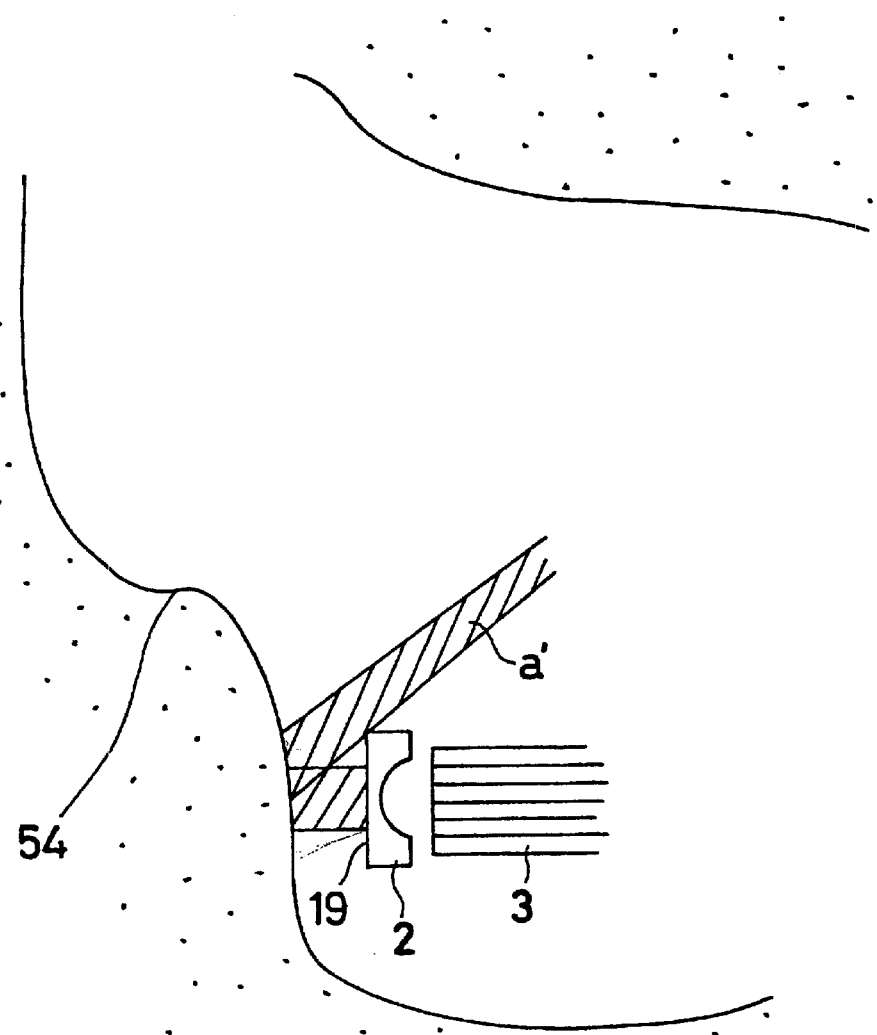
FIG. 7 illustrates the generation of a halation in the proximity part when observing a large intestine.
Figure 8:
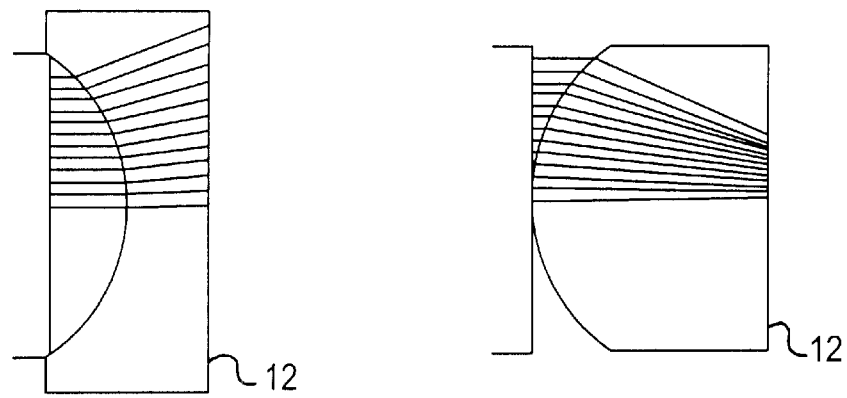
FIG. 8 is a light ray figure of parallel light-incidence on a concave lens and a convex lens.

The appearance at the time of an observation of proximity is shown in FIG. 7. The reflected luminous flux shown by oblique line part a' irradiates towards a wide-angle object optical system (Not shown) to produce a halation. It is the same as that in case of the observation of FIG. 4. As will be understood from FIG. 7, the emitted light from the nearly center section of the illumination lens 2 is a factor which causes a halation. In such a case, a position distribution (brightness distribution) of the light of the radiation surface of an illumination optical system needs to be equalised with a light distribution of an illumination optical system.

FIGS. 8(a) and (b) show light ray figures each having incidence light parallel with a concave lens with negative power and a convex lens with positive power, respectively.

From FIGS. 8(a) and (b), it is shown that the center part of the lens radiation surface 12 has a higher density of light rays in both of the optical systems. In other words, brightness is high and a nonuniformity of illumination exists. However, a halation is mitigable by using the illumination optical system 11'.

Figure 9A:
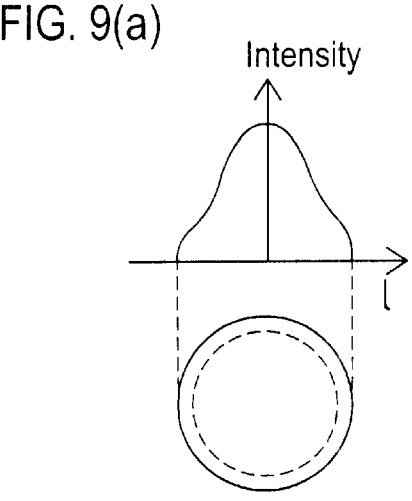
FIGS. 9(a) and 9(b) illustrate a brightness distribution of an illumination optical system radiation surface in the case where it consists only of a concave lens, and where a frosted glass is combined with a concave lens, respectively.

FIG. 9(a) shows a brightness distribution in an illumination optical system radiation surface in the case of the illumination optical system 11 which consists only of a concave lens. FIG. 9(a) shows a brightness distribution in an illumination optical system radiation surface in the case of the illumination optical system 11' which combines the frosted glass with the concave lens.

Figure 9B:
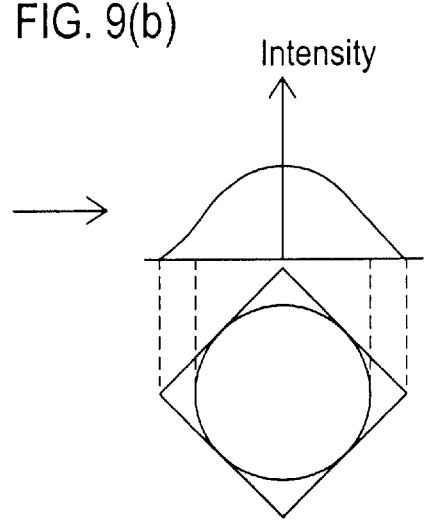

In the case of FIG. 9(b) which has the frosted glass, the difference between the optical system center and periphery of the optical system narrows, and the brightness distribution becomes more uniform.

Moreover, a brightness distribution is extended more by arranging a frosted glass which has a radiation surface whose effective area is larger than the end face of a light guide. Therefore, it is possible to reduce a halation under the observation conditions shown in FIG. 4.

The illumination lens 2 is not restricted to the spherical surface plane concave lens shown in FIG. 1. In order to obtain a more extensive light distribution, a lens which has an aspheric surface 13 shown in FIG. 10(a) and FIG. 10(c), and a lens which has a multi-stage curvature surface 14 may be used. Moreover, a lens which has concavity in both sides as shown in FIG. 10(b) may be used.

Figure 29A:
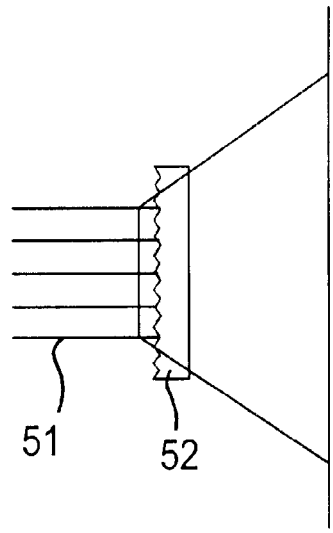
FIGS. 29(a) and 29(b) show a conventional endoscope illumination optical system.
Figure 29B:
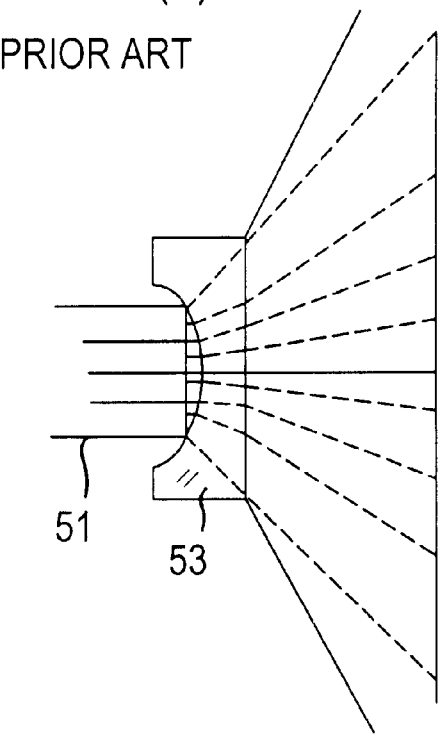
Figure 30:
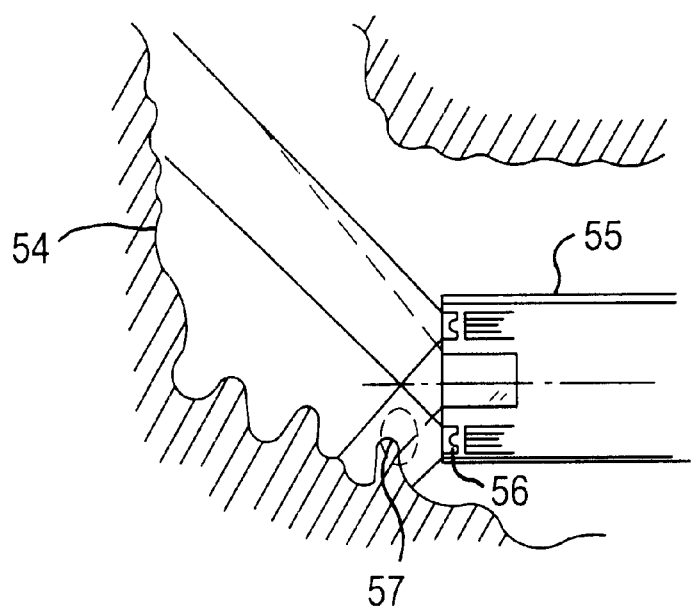
FIG. 30 shows a halation that is generated within a pipe having waviness.
Figure 31A:
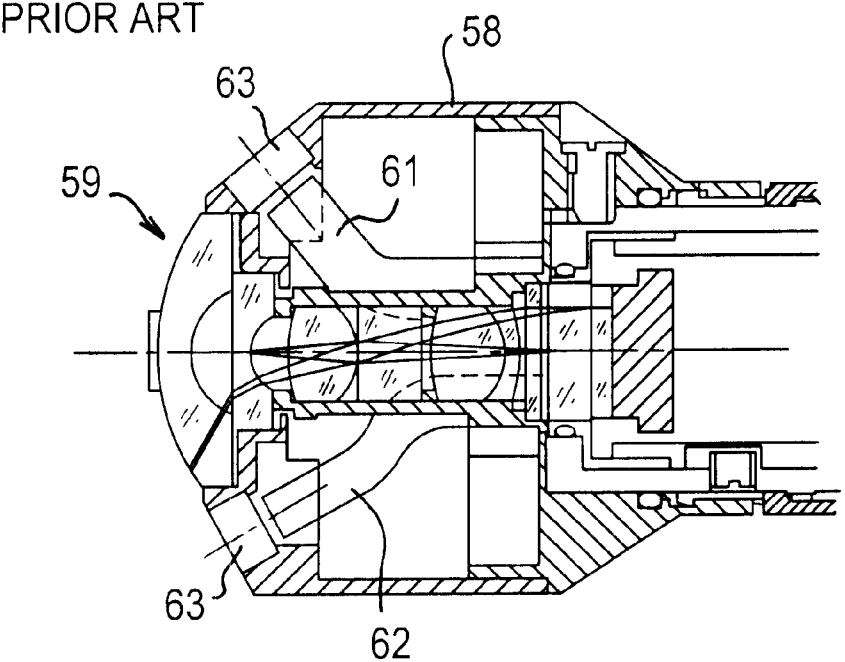
FIGS. 31(a) and 31(b) illustrate a technique for preventing a halation for a conventional endoscope.
Figure 31B:
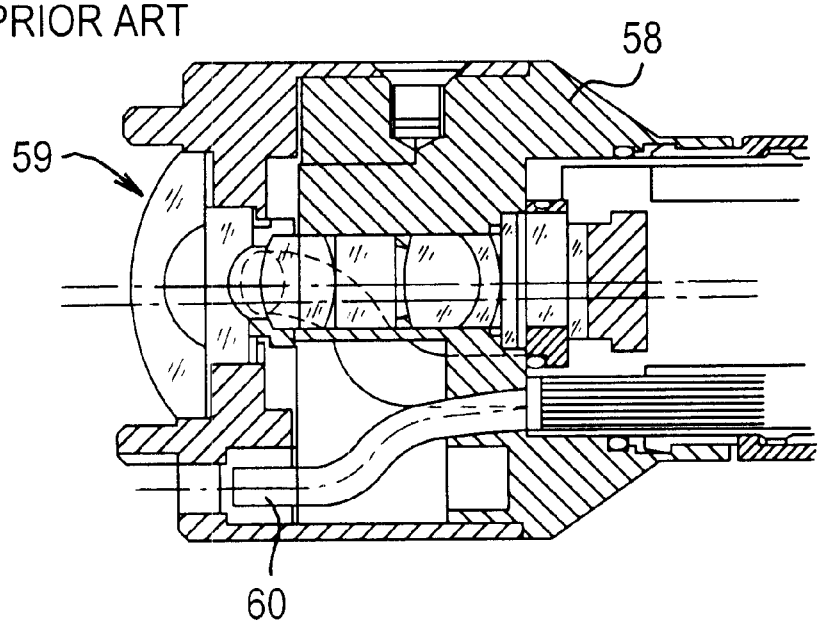

Generally, water drained off from the cleaning nozzle for cleaning an end part of the endoscope adheres on the surface of an illuminating system thereby deteriorating an illumination. Therefore, a flat surface or some convex surface is better than a concave shape surface. The illumination lens 2 of an endoscope uses an even concave type shown in FIG. 29(b). However, by making the radiation surface of the diffusion element (for example, a frosted glass) 4 into a flat surface, a biconcave lens, which has a concave surface on both sides as shown in FIG. 10(b), which strengthens negative power can be used. Moreover, a lens type with curvatures, such as a spherical surface 16 and a surface 14 with multi-stage curvatures to the core part of a rod lens 15 as shown in FIGS. 11(a) and (b) is also effective.

It is possible to return light leaked out of the lens on the lens side to illumination light by using a side lens having a mirror surface based on the difference of the refractive index of glass and air, or an adhesive agent.

A rod lens 15 tends to produce a color nonuniformity, but a color nonuniformity is not generated when the diffusion element 4 is arranged on the front.

As mentioned above, a lens type with difficult usage can also be used by having the diffusion element 4 at the end of a radiation side of the illumination lens 2.

Figure 12A:
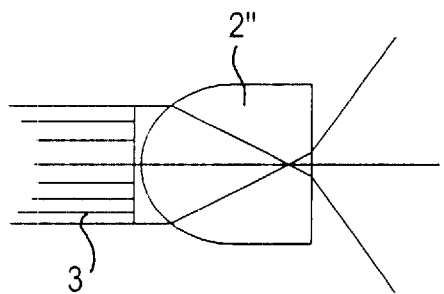
FIG. 12 shows the case where a convex lens is used as an illumination lens.
Figure 12B:
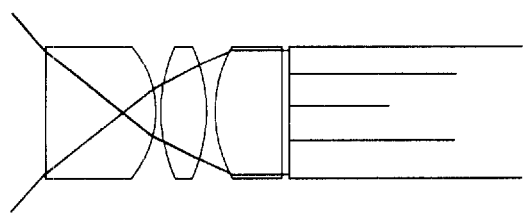
Figure 12C:
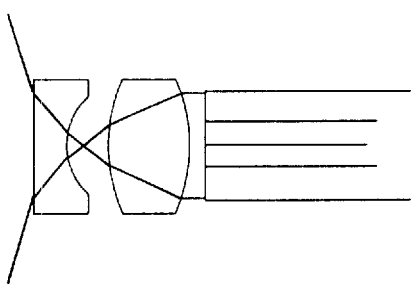
Figure 12D:
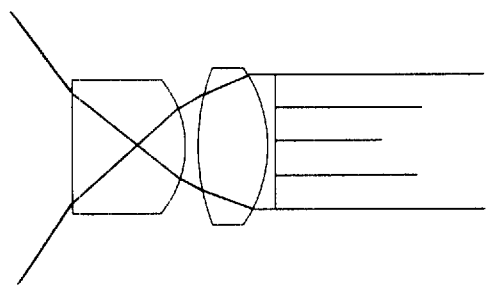

It is not restricted to lens 2' which has a negative power as above-mentioned description, but the effect is similar on convex lens 2" which has a positive power, which is shown in FIG. 12(a). Since convex lens 2" is a condensing optical system, a brightness distribution of the end face of light guide 3 tends to be projected on a photographed object, and tends to become a nonuniformity. However, since an image formation relationship collapses by the diffusion effect of the diffusion element 4, the nonuniformity is prevented. Also, the effect is similar the lenses by FIG. 12(b)-(d). The lenses means can be defined as a single-lens, plural single-lenses, or combination thereof.

In other words, by arranging the illumination lens 2 to spread light distribution, and having the diffusion element 4 at the end of a radiation side of the illumination lens 2 for blurring the pupil of the light radiated from a light guide 3, and further by equalising a brightness distribution at the radiation surface in an illumination optical system 11', a wide illumination range is obtained and a reduction of halation is performed.

The second embodiment, provides an endoscope comprising an object optical system and four illumination optical systems, with two or more types of illumination optical systems having different illumination strength and light distribution. When illuminating the visual field range the illumination optical system having the greater light distribution and illumination strength is arranged among the illumination optical systems at the end position of endoscope corresponding to both sides of a long side of a screen of the wide-angle object optical system.

At the end position of the endoscope corresponding to both sides of the direction of a short side of the screen of the wide-angle object optical system, the illumination optical system having a narrow light distribution and small illumination strength is arranged among the illumination optical systems.

To prevent the halation, the arrangement relationship of the object optical system and the illumination optical system in the end part of the endoscope is important.

Generally, in the case of the medical endoscope, the channel for inserting the surgical tool to perform a treatment etc. in the inside of the body, in addition to an object optical system and an illumination optical system, and the nozzle for cleaning the stain of an object optical system, etc. are arranged at the end of an endoscope.

One example of an end layout having two illumination optical systems 111 and 112 is shown in FIG. 13. Also shown in FIG. 13 is a channel 5 for a surgical tool, etc. and a nozzle 6 for cleaning the end surface of an endoscope.

In an another example, as shown in FIG. 14(b), the amount of emitted light from each illumination optical system 111–114 is dispersed by securing illumination light required for an observation from all the four illumination optical systems 111–114. Therefore, when one of the illumination optical systems 111–114 causes a halation, the quantity of light emitted from that illumination optical system is small compared with the amount of emitted light from the other three illumination optical systems. Therefore, as compared with the two illumination optical system shown in FIG. 14(a), the halation will be small.

FIG. 15(a) shows the state of a halation in the two illumination optical system of FIG. 14 (a), and FIG. 15(b) shows the state of a halation in the four illumination optical system of FIG. 14 (b). When observing a proximity, in the two illumination optical system as shown in FIG. 15(a), a large halation arises in the right and left direction (direction g of FIG. 16). A large part of a screen becomes white which makes observation very difficult. However, since the small white light is dispersed and generated by setting four illumination optical systems to 111–114 as shown in FIG. 15 (b), as compared with the case of two illumination, it becomes remarkably easy to observe an object.

Figure 16:
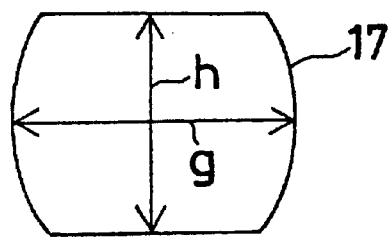
FIG. 16 illustrates a shape of an observation screen where the visual field range differs in the horizontal and vertical directions of a screen.

FIG. 16 shows a shape 17 of an observation screen where a visual field range differs in the g and h directions. Usually, since the larger direction g of a visual field range needs to illuminate the periphery, the quantity of illumination light must be increased. The direction h of the narrow upper and lower sides of a visual field range requires less illumination light than in the large direction g of a visual field range. However, by when illuminating the periphery more than necessary, a halation becomes easier to generate.

Figure 17:
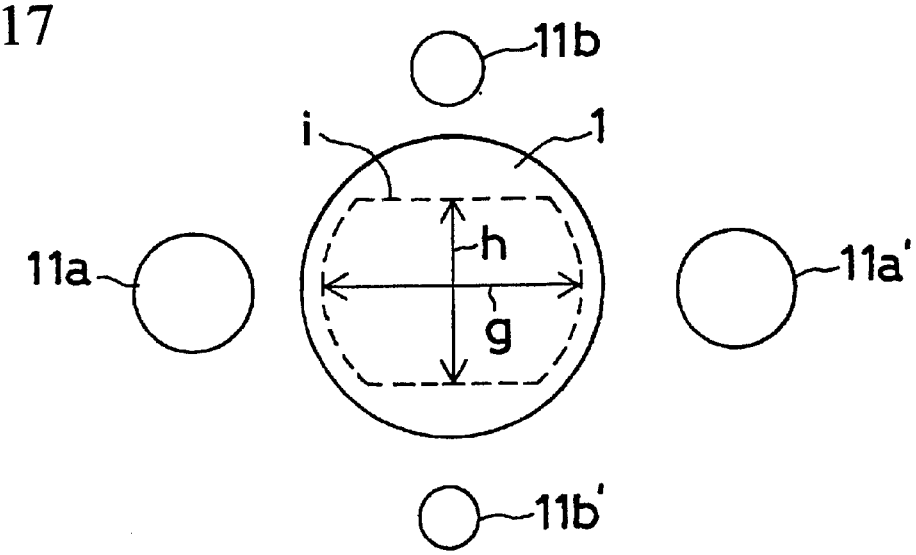
FIG. 17 shows an illumination optical system at the end of an endoscope according to the second embodiment of the present invention.

As shown in FIG. 17, a halation caused by illumination light which is not needed in an observation can be prevent by distributing the illumination light into optical system 11a and 11a' which radiate as much light as needed in the g direction of a visual field range, and by arranging illumination optical systems 11b and 11b' which radiate less light of in the narrow direction h of a visual field range.

In addition, dotted line i shows a range equivalent to screen 17 of FIG. 16 in the drawing.

Moreover, in such illumination optical systems 11a, 11a', 11b, and 11b', if a diffusion element is arranged at the end of an illumination lens radiation side as described in the first embodiment, a halation can be reduced further.

According to the third embodiment at the present invention, an endoscope comprising an object optical system and four illumination optical systems, wherein the four illumination optical systems have two or more types of illumination optical systems having different illumination strength and light distribution. The endoscope has a wide light distribution illumination optical system arranged at the end position corresponding to both sides of the direction of a long side of the screen by the object optical system, and an narrow light distribution illumination optical system arranged at the end position corresponding to the both sides of the direction of a short side of the screen by the object optical system.

Figure 18:
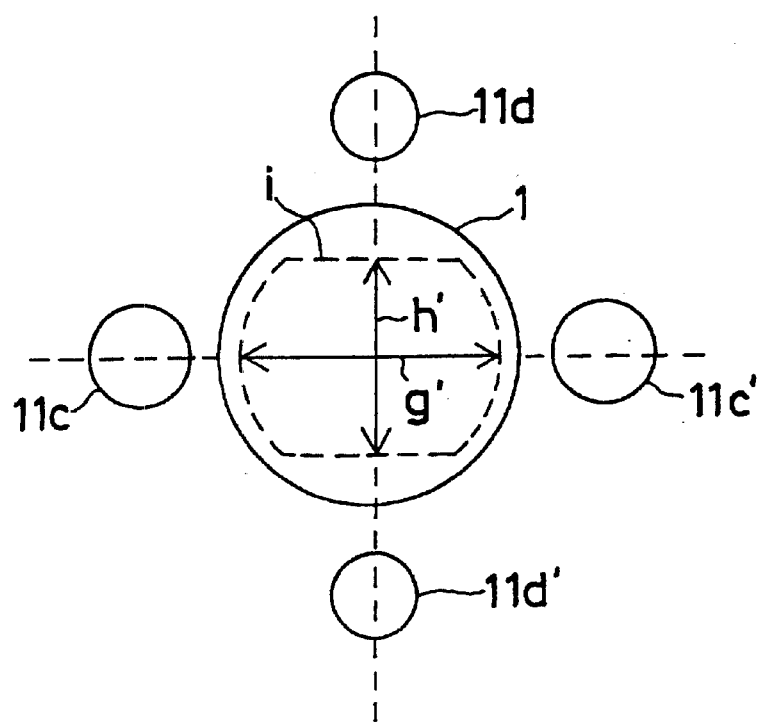
FIG. 18 shows an illumination optical system at the end of an endoscope according to the third embodiment of the present invention.

As shown in FIG. 18, illumination optical systems 11c and 11c' have a wide light distribution and illumination optical systems, and illumination optical systems 11d and 11d' have a light distribution narrower than that of illumination optical systems 11c and 11c'.

Figure 19:
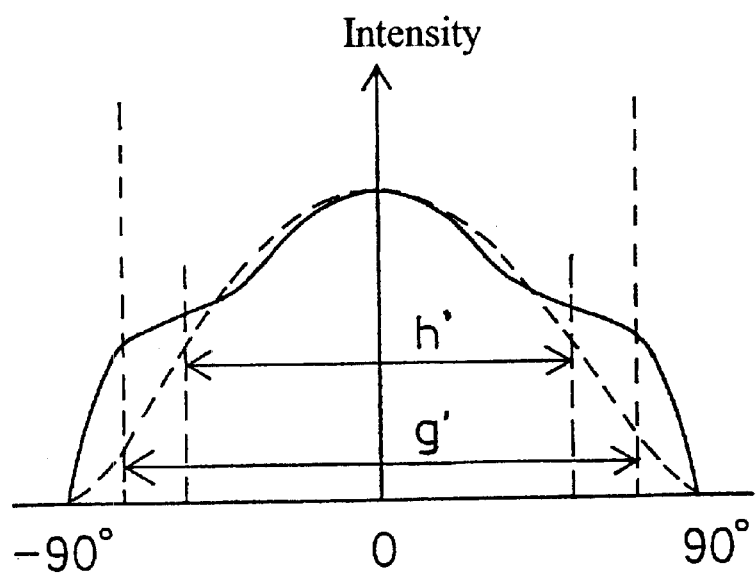
FIG. 19 shows a light distribution of all the illumination lights of the illumination optical system of FIG. 18.

FIG. 19 shows a light distribution for the illumination optical system 11c, 11c', 11d, 11d' shown in FIG. 18.

Figure 20:
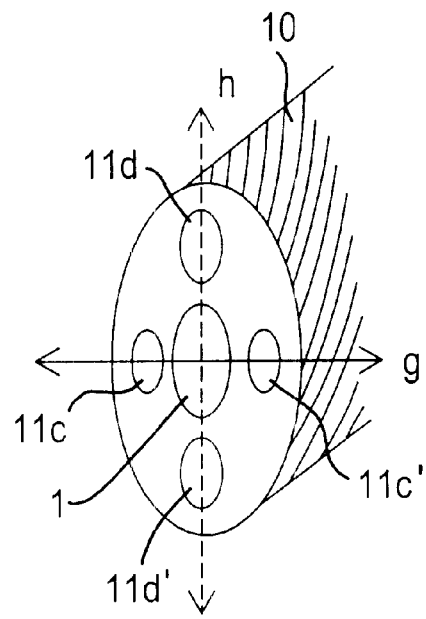
FIG. 20 is a perspective diagram of the leading end part of an endoscope according to the third embodiment.

FIG. 20 shows an end part 10 of endoscope with a continuous horizontal line g and a dotted vertical line h.

The visual field range of a screen in the horizontal direction g' needs to illuminate light in a wider distribution than in the vertical h' direction that is, an observation range can be illuminated without a nonuniformity as in the second embodiment. Therefore, a halation is reduced.

Figure 21A:
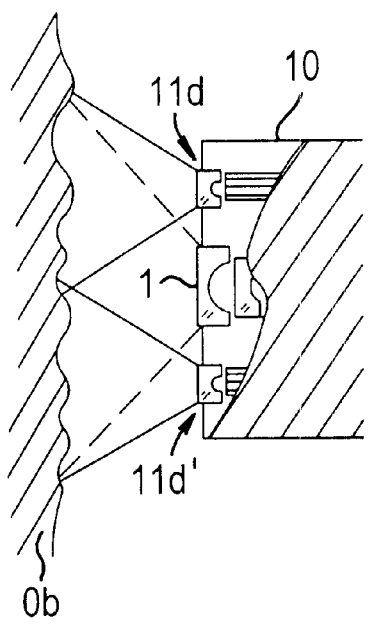
FIGS. 21(a) and 21(b) show an illumination range and an visual field range in the direction of the short side and long side of a screen, respectively.
Figure 21B:
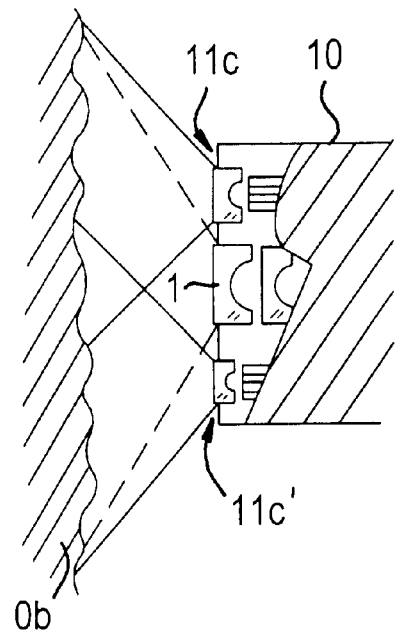

FIGS. 21(a) and 21(b) show an illumination range and an visual field range in the direction of the short and long side of a screen, respectively.

Moreover, if a diffusion element is arranged at the end of an illumination lens radiation side, as described in the first embodiment, in this illumination optical system, halations can be reduced further.

Figure 22:
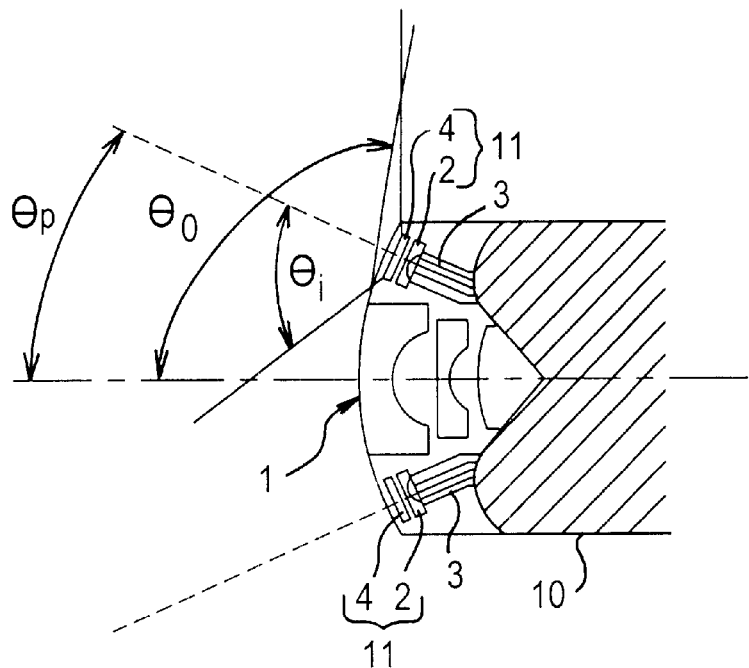
FIG. 22 is sectional drawing of the leading end part of an endoscope according to the fourth embodiment of the present invention.

An endoscope according to the fourth embodiment of the present invention is shown in FIG. 22.

In an endoscope in which the end of the endoscope has a streamline shape as a means to reduce a halation and to obtain a favorable observation state, the endoscope comprises an object optical system arranged on top of the streamline shape, an illumination optical system which consists of a lens system which has a power in the direction of a slope of the streamline shape, and a diffusion element arranged at the radiation side of the illumination optical system, wherein the following conditions are fulfilled.

$$1 < Ss/Si < 8 \quad (1)$$

$$\theta p < \theta i < \theta o - \theta p \quad (2)$$

wherein Ss is the effective area of the radiation surface of the diffusion element.

Si is the effective area of the plane of incidence of the illumination lens system.

θp is the angle between the optical axes of the object optical system and the illumination optical system.

θi is a half-angle of the light distribution angle of the emitted light from the illumination optical system.

θo is a half-angle of view of the object optical system.

FIG. 22 shows a cross section of the leading end part 10 of an endoscope according to this embodiment.

The object optical system 1 has a viewing angle which exceeds 180 degrees. To achieve this purpose, the end of the endoscope is stream lined and the object optical system 1 is disposed at the end of the streamline line shape end portion of the endoscope.

Moreover, the illumination optical system 11 is configured on a side of the streamline shape so that it does not interfere with the observation range.

In the endoscope which has such an arrangement relationship, in order to reduce a halation and to obtain a favorable observation state, it is desirable to satisfy the following conditional expressions.

$$1 < Ss/Si < 8 \quad (1)$$

$$\theta p < \theta i < \theta o - \theta p \quad (2)$$

Conditional expression (1) specifies the effect of the diffusion element 4. If it is less than the minimum 1, the halation-preventive effect becomes weaker and the objective of this invention can not be attained. On the other hand, if it exceeds the maximum 8, an end part 10 of the endoscope becomes thick, which is not preferable for an endoscope.

Conditional expression (2) defines the arrangement relationship of the object optical system 1 and the illumination optical system 10. If it is less than the minimum θp, it will cause trouble to an observation such that illumination light will not reach the longitudinal direction of an endoscope, and that the center of screen will become dark. On the other hand, when it exceeds the upper limit θo−θp, the illumination light irradiates to a wide-angle object system directly, which causes a flare and a halation, and the objective of this invention cannot be attained.

In an object optical system and an illumination optical system according to the fifth embodiment of the present invention, a diffusion element is respectively provided at the end of an illumination lens system. The diffusion element has a radiation surface with larger effective area than the plane of incidence of the illumination lens system, which reduces the effect of a halation.

In particular, the shape of a diffusion element does not need to be a similar shape as that of the illumination lens. It is sufficient that the diffusion element be larger than the plane of incidence of the illumination lens system. Therefore, as the image is blurred to diffuse, a halation is reduced. Therefore, a diffusion element of various shapes is suitable for the layout at the end of an endoscope.

Figure 23A:
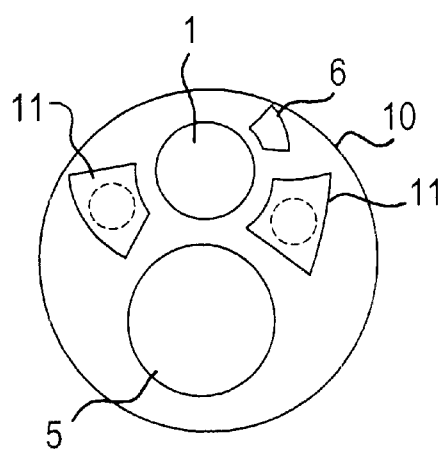
FIGS. 23(a) and 23(b) show an example of various layouts of an endoscope end according to the fifth embodiment of the present invention.
Figure 23B:
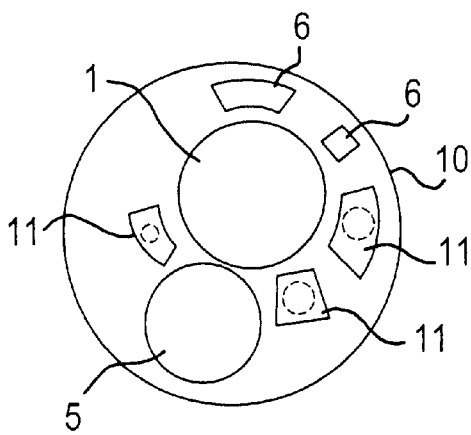
Figure 24A:
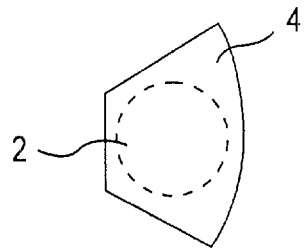
FIG. 24 illustrates the outer diameter of various lenses and diffusion element shapes.
Figure 24B:
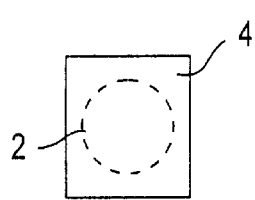
Figure 24C:
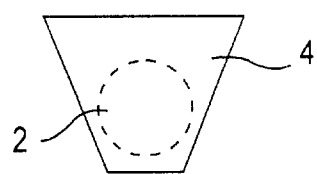
Figure 24D:
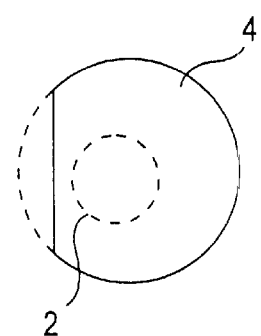
Figure 24E:
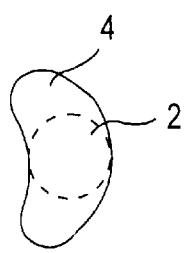
Figure 24F:
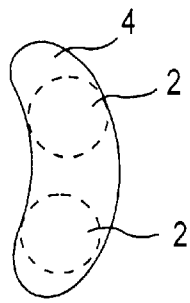

FIG. 23 shows an example of a layout. Generally, the outer diameter shape of a lens has many round shapes. If the diffusion element 4 is made of a similar shape to that of the lens, the outer diameter of the endoscope leading end part will become thick. Therefore, a diffusion element 4 which does not make the end outer diameter of an endoscope thicker can be configured by taking various shapes which are shown in FIGS. 24 (a)–(f), thereby reducing the dead space on an end layout.

In addition, in FIGS. 24(a)–(f), a dotted line shows the radiation surface for an illumination lens 2, and a continuous line shows the radiation surface of the diffusion element 4.

Figure 25:
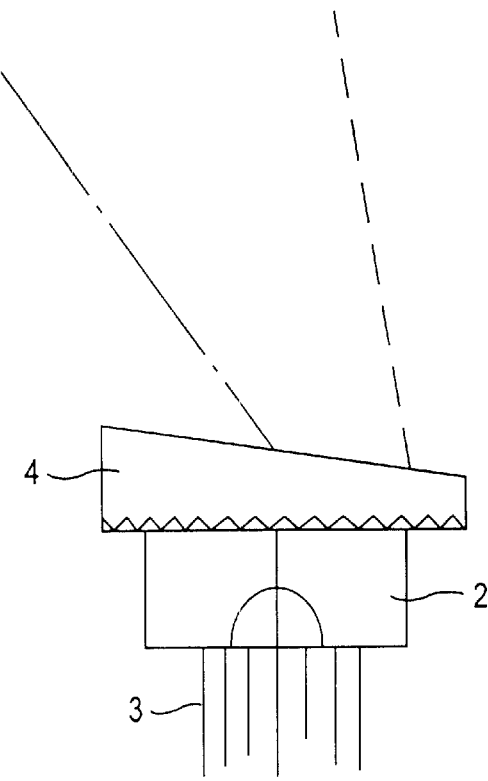
FIG. 25 shows the case where a diffusion element has a wedge shape.

Moreover, it is possible to change the direction of a light distribution by composing the diffusion element 4 in a wedge shape shown in FIG. 25, thereby bending the optical axis of an illumination optical system.

Generally, in the case of a medical endoscope, an object optical system, an illumination optical system, the channel for inserting the surgical tools for giving a treatment, etc., into the inside of the body, and the cleaning nozzle for cleaning the object optical system, etc., are arranged at the end of an endoscope. Therefore, the composition of above-mentioned second and third embodiments is suitable for obtaining a favorable illumination light which mainly reduces a halation.

However, in the case of the endoscope which has a channel, a cleaning nozzle, etc. at an end, since the object optical system and the illumination optical system are arranged in the cross shape, a dead space where nothing is located increases, and an outer diameter tends to become thick. To solve this problem it is desirable to make the endoscope thinner, as discussed in the sixth embodiment below.

Figure 26A:
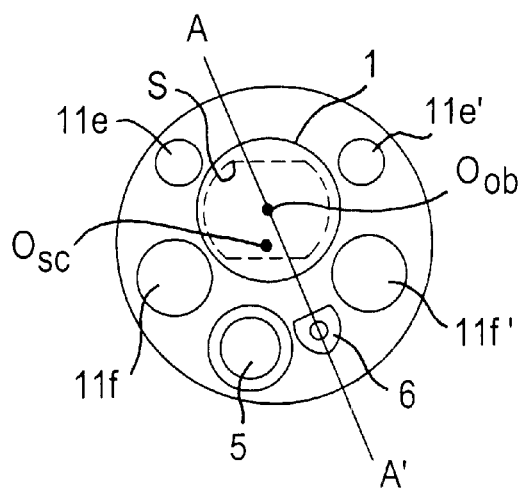
FIGS. 26(a) and 26(b) illustrate an illumination optical system at the end of an endoscope according to the sixth embodiment of the present invention.
Figure 26B:
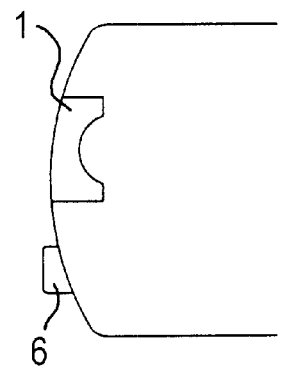

The front elevation at the end of an endoscope according to this embodiment is shown in FIG. 26(a). FIG. 26(b) shows the A–A' cross section in FIG. 26(a). The amount of emitted light from illumination optical systems 11e and 11e' is less than the amount of emitted light from of illumination optical systems 11f and 11f'. In this example, the endoscope also has smaller outer diameter.

The optical axis Oob of the object optical system 1 (dotted line S shows the range equivalent to a screen) and periphery center Osc in end of the endoscope become eccentric. Reference numeral 5 is a channel for surgical tool, or the like, and 6 is a nozzle for cleaning the end surface of the endoscope.

According to the arrangement of the illumination optical systems 11e, 11e', 11f and 11f' of FIG. 26, more light is radiated in the direction of the long side of the visual field range then in the direction of the short side. Therefore, favorable illumination can be obtained by the similar effect as above-mentioned in the second embodiment.

Moreover, the channel 5 and the nozzle 6 are approximately configured in the direction of the short side of the screen by performing eccentricity of the optical axis Oob of the object optical system 1 and the periphery center Osc in end of endoscope end, thus preventing the visual field eclipse by the nozzle etc.

In addition, illumination optical system 11e and 11e' with a small (the amount of emitted lights being small) outer diameter are arranged approximately opposite to channel 5 or the cleaning nozzle 6 with respect to the object optical system 1, thereby effectively using the space in end of the endoscope, and preventing the outer diameter from getting thick.

Figure 27:
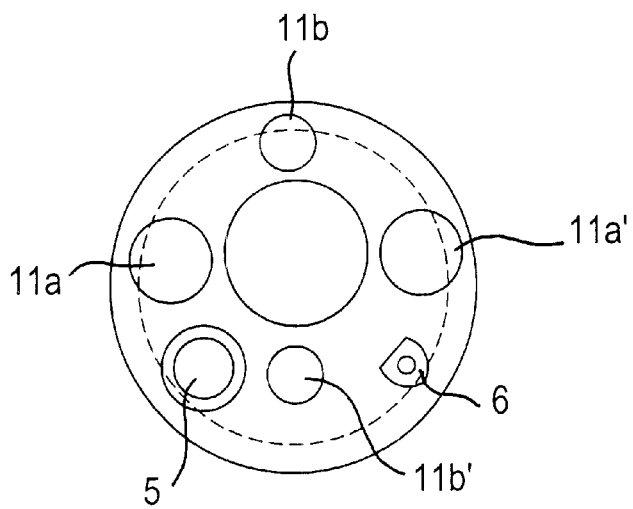
FIG. 27 shows channel and a nozzle at the end of an endoscope according to the second embodiment.

An arrangement with an object optical system and an illumination optical system according to the second embodiment, a channel 5 and a nozzle 6 are arranged as shown in FIG. 27.

In FIG. 27, the dotted line shows the outer radius of the in end of the endoscope illustrated in FIG. 26(a). In the case of FIG. 27, the dead space and the outer diameter tends to increase as compared to the endoscope of FIG. 26.

Figure 28A:
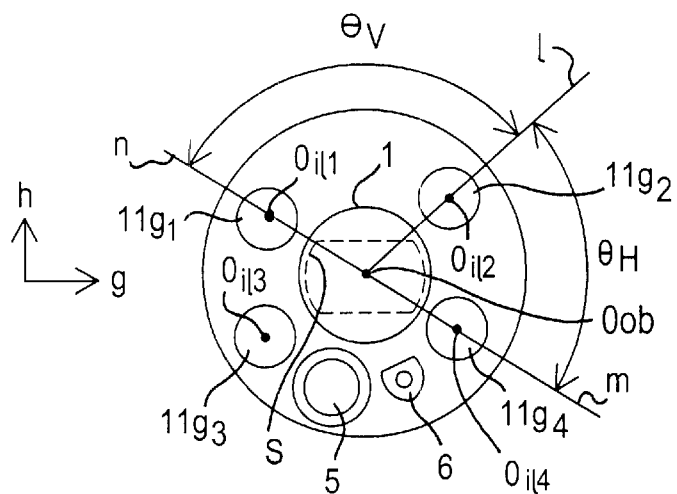
FIG. 28 shows an illumination optical system at the end of an endoscope according to the seventh embodiment of the present invention.
Figure 28B:
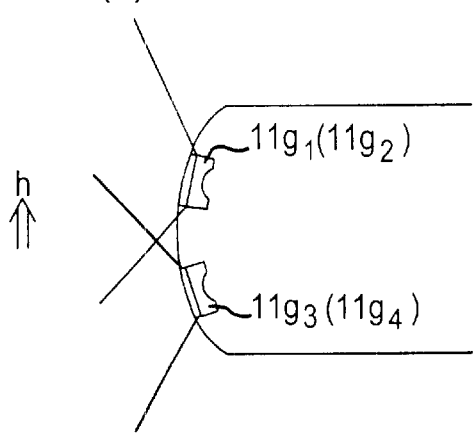
Figure 28C:
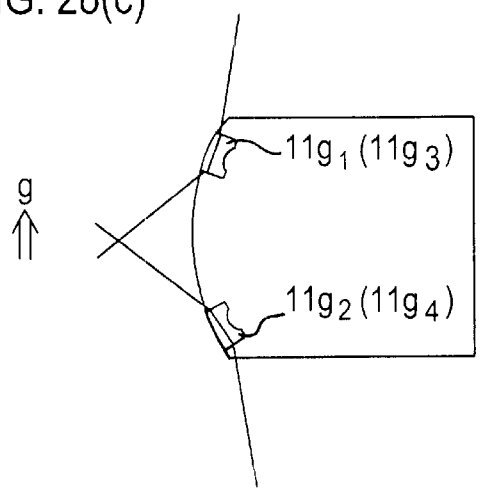

An endoscope end according to the seventh embodiment of the present invention is shown in FIG. 28(a). FIG. 28(b) shows the cross section in the h direction of the endoscope shown in FIG. 28(a). FIG. 28(c) shows the cross section in the g direction of the endoscope shown in FIG. 28(a).

Illumination optical systems 11g1, 11g2, 11g3, and 11g4 emit equal amount of light. Oil1, 0il2, and Oil3 and Oil4 express the centers of illumination optical systems 11g1, 11g2, 11g3, and 11g4, respectively. The endoscope shown in FIG. 28 further includes an object optical system 1 (dotted line S shows the range equivalent to a screen), channel 5 for surgical tool, or the like, and a nozzle 6 for washing the end surface.

Since the end of the endoscope according to this embodiment has a streamline shape, and spreads in the direction (g) of the long side of the screen, an illumination range (light distribution) differs between the direction of a long side and the direction of a short side of the screen. It turns out that the light distribution in the g direction is larger.

Specifically, as shown, when the angle between straight line 1 binding the optical axis Oob and the center Oil2 of the object optical system 1 and straight line m binding the optical axis Oob and the center Oil4 is set to θH, and the angle between straight line n binding the optical axis Oob and the center Oil1 of the object optical system 1 and straight line 1 is set to θV, by arranging the relationship θH<θV, the visual field range in the direction of the long side can be illuminated broadly compared with the range in the direction of the short side. Therefore, favorable illumination can be obtained by the similar effect as above-mentioned in the third embodiment.

In addition, also in this embodiment, the outer diameter is thinly restrained by configuring a channel and a nozzle like in the sixth embodiment.

As above demonstrated, this invention is effective in combination with a very wide-angle object optical system. A wide-angle object optical system which has a viewing angle exceeding 170 degrees is desirable. Specifically viewing angles of 180 degrees, 200 degrees, and 220 degrees, are advantageous in the medical field.

According to an endoscope of this invention, since an illumination optical system consists of a lens system which has a power, and a diffusion element arranged at the radiation side, a halation can be reduced and an illumination nonuniformity can be prevented even when an observed object is adjacent to the endoscope or has a high reflecting rate.

What is claimed is:

1. An endoscope apparatus for reducing a halation for a large observation area without an illumination nonuniformity, said endoscope apparatus comprising:

an insertion part having an end, said end having a wide-angle object optical system with two or more types of illumination optical systems having different illumination strength or light distribution;

wherein an illumination optical system having a greater illumination strength or wider light distribution is arranged on both sides of said end in a direction of a long side of a screen of the wide-angle object optical system, wherein an illumination optical system having a lesser illumination strength or narrower light distribution is arranged on both sides of said end in a direction of a short side of the screen of the wide-angle object optical system.

2. The endoscope apparatus according to claim 1, wherein the illumination optical systems include four illumination lenses.

3. The endoscope according to claim 1, wherein each of the illumination optical systems consist of a lens system which has a power and a diffusion element arranged at the object side.

4. The endoscope according to claim 3, wherein each of the illumination optical systems include a concave lens system which has a negative power and a diffusion element arranged at the object side.

5. The endoscope apparatus according to claim 3, wherein each of the illumination optical systems include a convex lens system which has a positive power and a diffusion element arranged at the object side.

6. The endoscope apparatus according to claim 4 or 5, wherein an effective area of a radiation surface of a diffusion element is larger than an effective area of a plane of incidence of the lens system.

7. The endoscope apparatus according to claim 1, wherein the end of an endoscope has a streamline shape and arranges an object optical system on the highest surface of linearity and includes a lens system with a power in a direction of a slope of the streamline shape and a diffusion element arranged at a radiation side.

8. The endoscope apparatus according to claim 7, wherein the following conditions are fulfilled:

$$1 < Ss/Si < 8 \tag{1}$$

$$\theta p < \theta i < \theta o - \theta p \tag{2}$$

wherein Ss is an effective area of a radiation surface of the diffusion element, Si is an effective area of a plane of incidence of the illumination lens system, θp is an angle between the optical axes of the object optical system and the illumination optical system, θi is a half-angle of a light distribution angle of emitted light from the illumination optical system, and θo is a half-angle of view of the object optical system.

9. An endoscope apparatus for reducing a halation for a large observation area without an illumination nonuniformity, said endoscope apparatus comprising:

a wide-angle object optical system having two or more types of illumination optical system with which illumination strength and light distribution differ, wherein an illumination optical system having a greater illumination strength and wider light distribution is arranged on both sides of an end part of said endoscope in a direction of a long side of a screen of the wide-angle object optical system, wherein an illumination optical system having a lesser illumination strength and narrower light distribution is arranged on both sides of said end in a direction of a short side of the screen of the wide-angle object optical system.

10. The endoscope apparatus according to claim 9, wherein the illumination optical systems include four illumination lenses.

11. The endoscope apparatus according to claim 9, wherein each of the illumination optical systems consist of a lens system which has a power and a diffusion element arranged at the object side.

12. The endoscope apparatus according to claim 11, wherein each of the illumination optical systems include a concave lens system which has a negative power and a diffusion element arranged at the object side.

13. The endoscope apparatus according to claim 11, wherein each of the illumination optical systems include a convex lens system which has a positive power and a diffusion element arranged at the object side.

14. The endoscope apparatus according to claim 12 or 13, wherein an effective area of a radiation surface of a diffusion element is larger than an effective area of a plane of incidence of the lens system.

15. The endoscope apparatus according to claim 9, wherein the end of an endoscope has a streamline shape and arranges an object optical system on the highest surface of linearity and includes a lens system with a power in a direction of a slope of the streamline shape and a diffusion element arranged at a radiation side.

16. The endoscope apparatus according to claim 15, wherein the following conditions are fulfilled:

$$1 < Ss/Si < 8 \tag{1}$$

$$\theta p < \theta i < \theta o - \theta p \tag{2}$$

wherein Ss is an effective area of a radiation surface of the diffusion element, Si is an effective area of a plane of incidence of the illumination lens system, θp is an angle between the optical axes of the object optical system and the illumination optical system, θi is a half-angle of a light distribution angle of emitted light from the illumination optical system, and θo is a half-angle of view of the object optical system.

* * * * *